US00PP31058P3

(12) United States Plant Patent
Moen

(10) Patent No.: US PP31,058 P3
(45) Date of Patent: Nov. 12, 2019

(54) ***GERBERA* PLANT NAMED 'GARSWEETMEMO'**

(50) Latin Name: *Gerbera hybrida*
Varietal Denomination: Garsweetmemo

(71) Applicant: Melchior Moen, Mijdrecht (NL)

(72) Inventor: Melchior Moen, Mijdrecht (NL)

(73) Assignee: Florist Holland B.V., Aalsmeer (NL)

( * ) Notice: Subject to any disclaimer, the term of this patent is extended or adjusted under 35 U.S.C. 154(b) by 0 days.

(21) Appl. No.: 15/932,281

(22) Filed: Feb. 16, 2018

(65) Prior Publication Data

US 2018/0255688 P1 Sep. 6, 2018

Related U.S. Application Data

(60) Provisional application No. 62/600,830, filed on Mar. 3, 2017.

(51) Int. Cl.
*A01H 5/02* (2018.01)
*A01H 6/14* (2018.01)

(52) U.S. Cl.
USPC ..... Plt./357
CPC ..... *A01H 6/1456* (2018.05)

(58) Field of Classification Search
USPC ..... Plt./357
CPC . A01H 5/02; A01H 5/025; A01H 5/00; A01H 6/14; A01H 6/1456
See application file for complete search history.

(56) References Cited

PUBLICATIONS

Kernock Park Plants Gerber GARVINEA 'Sweet Memories', retrieved on Feb. 4, 2019, retrieved from the Internet at https://www.kernock.co.uk/acatalog/Gerbera-Garvinea-Sweet-Memories-P-U4677.html, 4 pp. (Year: 2019).*

Meadowlands Horticultural Inc. 2016-2017 *Gerbera* Program, retrieved on Jan. 30, 2019, retrieved from the Internet at http://www.meadowlandsinc.com/wp-content/uploads/2015/07/2017-MHI-Gerbera-Program-US.pdf, pp. 1-8. (Year: 2017).*

Rice. Chelsea Plant of the Year. The Plantsman 2016, retrieved on Feb. 4, 2019, retrieved from the Internet at https://www.rhs.org.uk/about-the-rhs/publications/magazines/the-plantsman/2016-Issues/September/chelsea-plant-of-the-year.pdf, pp. 188-195. (Year: 2016).*

Yu et al. Organ identity genes and modified patterns of flower development in *Gerbera hybrida* (*Asteraceae*) The Plant Journal (1999) 17(1), 51-62. (Year: 1999).*

* cited by examiner

*Primary Examiner* — June Hwu
(74) *Attorney, Agent, or Firm* — C. A. Whealy

(57) ABSTRACT

A new and distinct cultivar of *Gerbera* plant named 'Garsweetmemo', characterized by its compact, broadly upright and uniformly mounding plant habit; dense and bushy appearance; numerous inflorescences with pink-colored ray florets; upright and strong scapes; and good garden performance.

1 Drawing Sheet

Botanical designation: *Gerbera hybrida.*
Cultivar denomination: 'GARSWEETMEMO'.

BACKGROUND OF THE INVENTION

The present invention relates to a new and distinct cultivar of *Gerbera* plant, botanically known as *Gerbera hybrida* and hereinafter referred to by the cultivar name 'Garsweetmemo'.

The new *Gerbera* plant is a product of a planned breeding program conducted by the Inventor in De Kwakel, The Netherlands. The objective of the breeding program is to create new compact garden *Gerbera* plants with numerous attractive inflorescences, resistant to cold temperatures and good garden performance.

The new *Gerbera* plant originated from a cross-pollination made during the spring of 2011 in De Kwakel, The Netherlands of a proprietary selection of *Gerbera hybrida* identified as code number 11T0675, not patented, as the female, or seed, parent with a proprietary selection of *Gerbera hybrida* identified as code number 07T029, not patented, as the male, or pollen, parent. The new *Gerbera* plant was discovered and selected by the Inventor as a single flowering plant within the progeny of the stated cross-pollination in a controlled greenhouse environment in De Kwakel, The Netherlands during the summer of 2012.

Asexual reproduction of the new *Gerbera* plant by vegetative stem cuttings in a controlled environment in De Kwakel, The Netherlands since the autumn of 2013 has shown that the unique features of this new *Gerbera* plant are stable and reproduced true to type in successive generations.

SUMMARY OF THE INVENTION

Plants of the new *Gerbera* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Garsweetmemo'. These characteristics in combination distinguish 'Garsweetmemo' as a new and distinct *Gerbera* plant:

1. Compact, broadly upright and uniformly mounding plant habit.

2. Dense and bushy appearance.
3. Numerous inflorescences with pink-colored ray florets.
4. Upright and strong scapes.
5. Good garden performance and relatively tolerant to cold temperatures.

Plants of the new *Gerbera* differ primarily from plants of the female parent selection in the following characteristics:

1. Plants of the new *Gerbera* have darker green-colored leaves than plants of the female parent selection.
2. Plants of the new *Gerbera* have larger inflorescences than plants of the female parent selection.
3. Inflorescences of plants of the new *Gerbera* have more ray florets than inflorescences of plants of the female parent selection.

Plants of the new *Gerbera* differ primarily from plants of the male parent selection in inflorescence size as plants of the new *Gerbera* have larger inflorescences than plants of the male parent selection.

Plants of the new *Gerbera* can be compared to plants of the *Gerbera hybrida* 'Garheart', disclosed in U.S. Plant Pat. No. 28,031. Plants of the new *Gerbera* differ from plants of 'Garheart' in the following characteristics:

1. Inflorescences of plants of the new *Gerbera* have more ray florets than inflorescences of plants of 'Garheart'.
2. Ray florets of plants of the new *Gerbera* are lighter pink in color than ray florets of plants of 'Garheart'.

BRIEF DESCRIPTION OF THE PHOTOGRAPH

The accompanying photograph illustrates the overall appearance of the new *Gerbera* plant showing the colors as true as it is reasonably possible to obtain in colored reproductions of this type. Colors in the photograph may differ slightly from the color values cited in the detailed botanical description which accurately describe the colors of the new *Gerbera* plant.

The photograph comprises a side perspective view of a typical flowering plant of 'Garsweetmemo' grown in a container.

DETAILED BOTANICAL DESCRIPTION

The aforementioned photograph and following observations and measurements describe plants grown during the autumn and winter in 19-cm containers in a glass-covered greenhouse in De Kwakel, The Netherlands and under cultural practices typical of commercial garden *Gerbera* production. During the production of the plants, day temperatures ranged from 12° C. to 15° C. and night temperatures averaged 12° C. Plants were six months old when the photograph was taken and 20 weeks old when the description was taken. In the following description, color references are made to The Royal Horticultural Society Colour Chart, 2015 Edition, except where general terms of ordinary dictionary significance are used.

Botanical classification: *Gerbera hybrida* 'Garsweetmemo'.

Parentage:

*Female, or seed, parent.*—Proprietary selection of *Gerbera hybrida* identified as code number 11T0675, not patented.

*Male, or pollen, parent.*—Proprietary selection of *Gerbera hybrida* identified as code number 07T029, not patented.

Propagation:

*Type.*—By cuttings and meristem culture.

*Time to initiate roots, by cuttings, summer and winter.*—About 3.5 weeks at temperatures about 20° C.

*Time to initiate roots, by tissue culture, summer and winter.*—About 2.5 to 3 weeks at temperatures about 20° C.

*Time to produce a rooted young plant, by cuttings, summer and winter.*—About 3.5 weeks at temperatures about 20° C. to 26° C.

*Time to produce a rooted young plant, by tissue culture, summer and winter.*—About five to six weeks at temperatures about 20° C.

*Root description.*—Fibrous; white in color.

Plant description:

*Appearance.*—Herbaceous perennial that is typically grown as a container or garden plant; compact and uniformly mounding plant habit; upright, broadly spreading and roughly flattened globular in shape; numerous leaves arranged in basal rosettes; dense and bushy habit; inflorescences held above the foliar plane on erect and strong basal scapes; moderately vigorous growth habit.

*Plant height, soil level to top of foliar plane.*—About 25 cm.

*Plant height, soil level to top of inflorescences.*—About 36.5 cm.

*Plant width.*—About 52 cm.

Leaf description:

*Arrangement.*—Alternate, simple.

*Length.*—About 23.6 cm.

*Width.*—About 7.8 cm.

*Shape.*—Oblanceolate to narrowly obovate; runcinate; slightly curved.

*Apex.*—Obtuse.

*Base.*—Acuminate.

*Margin.*—Coarsely and irregularly angulate; sinuses medium to deep and divergent; moderately undulate.

*Texture and luster, upper surface.*—Glabrous, smooth; moderately glossy.

*Texture and luster, lower surface.*—Moderately to densely pubescent, slightly rugose; matte.

*Venation pattern.*—Pinnate.

*Color.*—Developing leaves, upper surface: Close to between 141A and 147A. Developing leaves, lower surface: Close to between 138A and 147B. Fully expanded leaves, upper surface: Close to NN137A; venation, close to 144A to 144B. Fully expanded leaves, lower surface: Close to 147B; venation, close to 144A.

*Petioles.*—Length: About 7.2 cm. Diameter: About 3 mm. Texture and luster, upper and lower surfaces: Moderately pubescent; slightly glossy. Strength: Moderate to strong. Color, upper surface: Close to 144A. Color, lower surface: Close to 144A to 144B.

Inflorescence description:

*Appearance.*—Single composite inflorescence form with oblanceolate-shaped ray florets; solitary inflorescences borne on upright and strong scapes and held above the foliar plane; ray, trans and disc florets arranged acropetally on a capitulum; inflorescences face upright.

*Fragrance.*—None detected.

*Flowering season.*—Plants begin flowering about three months after planting; under garden conditions in The Netherlands, plants flower from spring to autumn; plants can be flowered year-round in the greenhouse.

*Inflorescence longevity.*—Depending on the temperature, inflorescences last about three weeks on the plant; inflorescences persistent.

*Quantity of inflorescences.*—Freely flowering habit with about 16 open and developing inflorescences per plant at one time.

*Inflorescence buds.*—Height: About 2.2 cm. Diameter: About 2.6 cm. Shape: Roughly globular. Texture and luster: Moderately pubescent; slightly glossy. Color: Close to 143B; immature ray florets, close to 176C and 176D.

*Inflorescence size.*—Diameter: About 7.7 cm. Depth (height): About 2.9 cm. Diameter of disc: About 3.6 cm. Receptacle height: About 4 mm. Receptacle diameter: About 5 mm. Receptacle color: Close to 157D.

*Ray florets.*—Quantity and arrangement: About 60 per inflorescence arranged in about three whorls. Orientation: Proximally, about 55° from vertical; distally, close to horizontal. Length: About 3.5 cm. Width: About 7.5 mm. Shape: Oblanceolate. Apex: Finely emarginate to finely praemorse. Base: Narrowly cuneate. Margin: Entire. Texture and luster, upper surface: Smooth, glabrous; velvety; longitudinally ridged; matte. Texture and luster, lower surface: Smooth, glabrous; moderately velvety; longitudinally ridged; slightly glossy. Color: When opening, upper surface: Close to 48C. When opening, lower surface: Close to 181C; fading towards the base, close to 174C. Fully opened, upper and lower surfaces: Close to slightly lighter than 48C; distally, close to 48D; color becoming closer to 54C and proximally, close to 59D, with development.

*Disc and trans florets.*—Quantity and arrangement: About 300 massed at center of receptacle in about eleven whorls. Length: About 2.1 cm. Width: About 9 mm. Shape: Tubular with upper two narrow free lobes and one broader free lobe. Apex: Acute; upper 50%, free. Base: Lower 50%, fused. Margin, free lobes: Entire. Texture, upper surface: Smooth, glabrous; slightly velvety; matte. Texture, lower surface: Smooth, glabrous; very slightly velvety; slightly glossy. Color: When opening, inner and outer surface: Close to 4D. Fully opened, inner and outer surface: Proximally, close to 155B; distally, close to NN155D.

*Pappus.*—Quantity of hairs per floret: About 60. Length: About 7 mm. Diameter: Less than 1 mm. Texture and luster: Soft; matte. Color: Close to 162D; distally, lighter than 162D.

*Phyllaries.*—Quantity and arrangement: About 50 per inflorescence arranged in about three whorls. Length: About 1.7 cm. Width (at base): About 2.5 mm. Shape: Ligulate. Apex: Narrowly acute. Base: Cuneate. Margin: Entire. Texture and luster, upper surface: Smooth, glabrous; moderately glossy. Texture and luster, lower surface: Sparsely to moderately pubescent; slightly glossy. Color, upper surface: Close to 143C. Color, lower surface: Close to 143A to 143B.

*Scapes.*—Length: About 35.5 cm. Diameter: Proximally, about 5 mm; distally, about 4 mm. Strength: Moderately strong. Angle: About 10° from vertical. Texture and luster: Moderately to densely pubescent; moderately glossy. Color: Proximally, close to 144A to 144B; distally, close to 147B.

*Reproductive organs.*—Androecium (present on disc florets only): Quantity per floret: Five. Filament length: About 7 mm. Filament color: Close to 150D. Anther shape: Ligulate; basifixed. Anther size: About 4 mm by 0.3 mm. Anther color: Close to 13A. Pollen amount: Scarce to moderate. Pollen color: Close to 13B. Gynoecium (present only on ray and disc florets): Quantity per floret: One. Pistil length: About 1.1 cm. Stigma diameter: About 0.5 mm. Stigma shape: Cleft. Stigma color: Close to NN155A. Style length: About 1 cm. Style color: Close to NN155D. Ovary color: Close to 157D.

*Seeds and fruits.*—Seed and fruit production has not been observed on plants of the new *Gerbera* to date.

Disease & pest resistance: Resistance to pathogens and pests common to *Gerbera* plants has not been observed on plants of the new *Gerbera* grown under commercial production conditions to date.

Garden performance: Plants of the new *Gerbera* have been observed to have good garden performance and to tolerate high temperatures about 35° C. and to be cold hardy to USDA Hardiness Zone 7.

It is claimed:

1. A new and distinct *Gerbera* plant named 'Garsweetmemo' as illustrated and described.

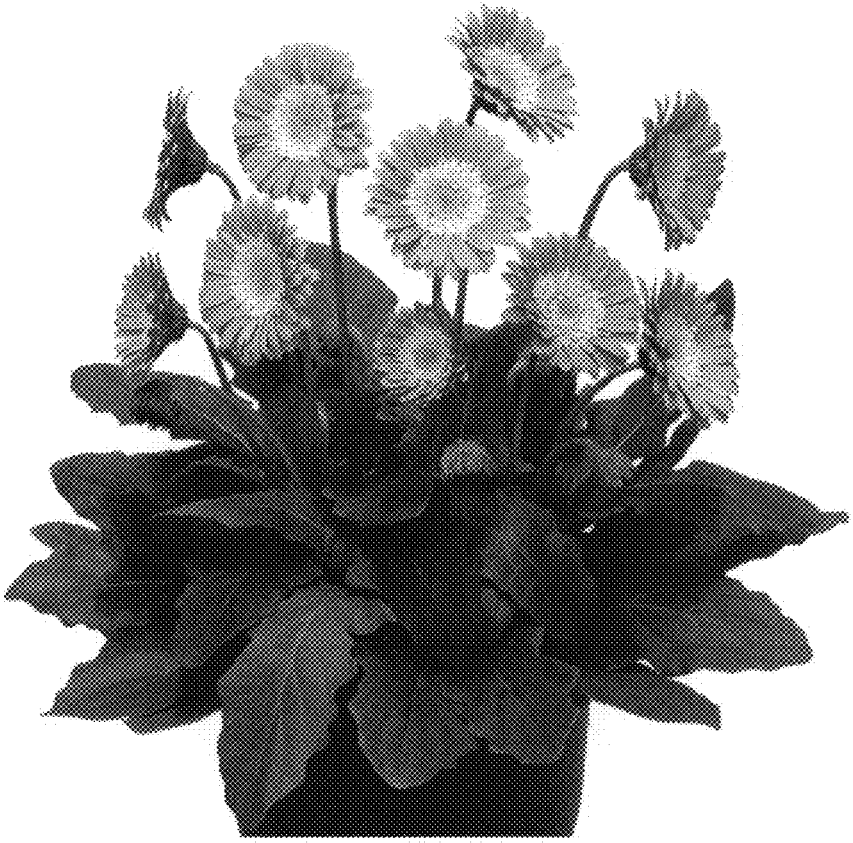

* * * * *